(12) United States Patent
Koops et al.

(10) Patent No.: US 8,868,156 B1
(45) Date of Patent: Oct. 21, 2014

(54) OPTICAL SPECTROSCOPY DEVICE AND METHOD FOR ITS MANUFACTURE

(75) Inventors: Hans W. P. Koops, Ober-Ramstadt (DE); Andreas Reinhardt, Hainburg (DE)

(73) Assignee: Deutsche Telekom AG, Bonn (DE)

( * ) Notice: Subject to any disclaimer, the term of this patent is extended or adjusted under 35 U.S.C. 154(b) by 1727 days.

(21) Appl. No.: 10/149,045

(22) PCT Filed: Nov. 22, 2000

(86) PCT No.: PCT/EP00/11618
§ 371 (c)(1),
(2), (4) Date: Oct. 9, 2002

(87) PCT Pub. No.: WO01/40777
PCT Pub. Date: Jun. 7, 2001

(30) Foreign Application Priority Data

Dec. 1, 1999 (DE) .................................. 199 57 682

(51) Int. Cl.
*A61B 5/00* (2006.01)
(52) U.S. Cl.
USPC ............................ 600/473; 600/407; 600/476
(58) Field of Classification Search
USPC ......... 356/328, 310–330, 451, 300, 326, 319; 128/630–633; 438/31, 32
See application file for complete search history.

(56) References Cited

U.S. PATENT DOCUMENTS

| | | | |
|---|---|---|---|
| 5,002,392 A | 3/1991 | Swope et al. | |
| 5,116,122 A | 5/1992 | Fukuma | |
| 5,493,393 A | 2/1996 | Beranek et al. | |
| 5,550,375 A | 8/1996 | Peters et al. | |
| 5,833,603 A | * 11/1998 | Kovacs et al. | 600/317 |
| 5,861,626 A | 1/1999 | Chandra et al. | |

FOREIGN PATENT DOCUMENTS

| | | |
|---|---|---|
| DE | 196 09 916 | 9/1997 |
| DE | 196 26 969 | 1/1998 |
| DE | 197 45 324 | 4/1999 |
| EP | 0 709 659 | 5/1996 |
| EP | 0 800 065 | 10/1997 |
| WO | WO 98/53284 | 11/1998 |
| WO | WO 99/03021 | 1/1999 |
| WO | WO 99/53350 | * 10/1999 |

OTHER PUBLICATIONS

Yee, Gaylin M., et al., "Miniature spectrometers for biochemical analysis"; Sensors and Actuators, vol. 58, 1997, pp. 61-66.
Mueller, C. and Mohr, J., "Microspectrometer Fabricated by the Liga Process"; Interdisciplinary Science Reviews, 1993, vol. 18, No. 3, pp. 273-279.

(Continued)

*Primary Examiner* — Peter Luong
(74) *Attorney, Agent, or Firm* — Kenyon & Kenyon LLP

(57) ABSTRACT

A device (1) for use in optical spectroscopy and a method for its manufacture are described. The device includes at least one light source (8) and at least one spectrometer (3) fabricated integratively, the optical components of the at least one spectrometer (3) being optical microcomponents (11,13,16, 19,20,21) which are mounted integratively on the top and/or bottom side (9,12) of a substrate board (2). In the method according to the present invention, at least one light source (8) is mounted on a substrate board (2), and at least one spectrometer (3) is produced monolithically in a three-dimensional integration on the substrate board (2). In this context, the spectrometer (3) that is produced according to the method is assembled from optical microcomponents (11,13,16,19,20, 21).

19 Claims, 2 Drawing Sheets

(56) References Cited

OTHER PUBLICATIONS

Figure 1:
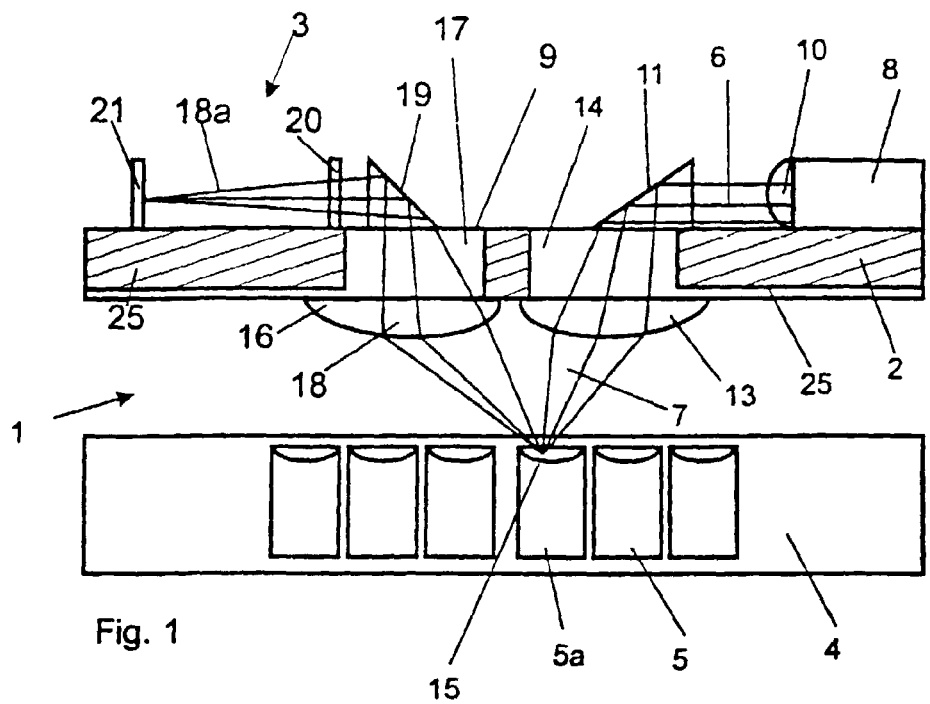

Sander, Dietmar and Muller, Jorg, "Breitbandiges optisches Mikrospektrometer als Mikroanalysesystem"; tm—Technisches Messen, 64, 1997, 4, pp. 143-146.

Menz, Wolfgang, "Die industrielle Anwendung der Mikrosystemtechnik"; atp—Automatisierungstechnische Praxis 37, 1995, 11, pp. 12-22.

* cited by examiner

OPTICAL SPECTROSCOPY DEVICE AND METHOD FOR ITS MANUFACTURE

The present invention is directed to a device for use in optical spectroscopy and to a method for its manufacture.

Numerous optical spectroscopy devices are known which can be used for various spectroscopic methods. In these devices essentially made up of optical spectrometers, the optical radiation to be analyzed can be excited by various physical processes of the substances to be analyzed. Such excitation processes can be of the thermal, electrical, and/or optical type. The devices necessary for this, such as those of a light source, can be contained both in the spectrometers themselves, but also provided externally thereto.

Depending on the substances to be analyzed, specific conditions must be able to be fulfilled, for instance with respect to the spectral region to be analyzed or the excitation energy to be applied.

Thus, for example, in the pharmaceutical industry, optical spectroscopy is increasingly being used for chemical reactions, to verify when new active substances are produced. In this context, essentially fluorescence radiation is analyzed.

Because of the multiplicity of possible reaction products produced by chemically reacting new as well as known substances with each other, efficient analysis devices and/or methods are sought. Moreover, due to this multiplicity, an ever smaller quantity is selected to be available for an analysis. Thus, it is already known to fill reaction vessels positioned in a row-type or planar array, in the form of saucers having a volumetric capacity of about $1 \times 10^{-6}$ l, with reagents. In this context, the up to a few thousand saucers of a test row are filled with the reagents using automated micropipettes. The reagents are used, in part, in small quantities, for instance in the range of $10^{-12}$ l.

These saucers are then observed using optical measuring methods and measured with respect to a specific reaction product. The existence of a reaction is ascertained in the process by observing fluorescing molecules that were attached to the reagents. One determines whether the reaction took place by measuring the reaction rate of the molecules of the reaction product. In this context, the measured displacement can be ascertained, for instance, by subjecting the reaction vessel to a defined luminous exposure. The time duration of the emission of such a fluorescence radiation is measured, for example, by taking a time measurement of the fluorescent light obtained following spectrometric decomposition. From this, inferences are made regarding the reaction that took place and the reaction products obtained. The measurement is performed in a computer-controlled operation and, in this context, the measuring system is moved from reaction volume to reaction volume, i.e., the array of reaction vessels is moved along under a microscope.

As measuring systems, one uses macroscopic fluorescence microscopes having illumination lasers, classic illumination and in-line imaging optics, including beam splitters and subsequent spectrometers. However, due to their massive design, measuring systems of this kind, as described by G. Gradi et al. in Bio Methods, vol. 10, pp. 331-351, Birkhäuser Publishers Basel and by S. Sterrer in J. of Receptor and Signal Transduction Research, vol. 17, 1997, pp. 511-520, limit the application to an only very limited reaction space.

From EP-A 2-0709659, one can infer a miniaturized, integrated spectrometer, where the objective is to accommodate all components, including the radiation source, of the detector and the control electronics on one single substrate.

In addition, from WO 99/53350, one can infer a monolithic infrared spectrometer, which includes a waveguide produced from silicon, which is designed to include the necessary components for performing an analysis, such as the reflector [mirror] and a grating. However, it is not used for the analysis of visible light, since silicon is non-transparent in the visible region.

The object of the present invention is, therefore, to provide an optical spectroscopy device, in particular a fluorescence spectrometer, whose dimensions will be adaptable to the increasingly smaller reaction volumes to be analyzed, and which, because of its design, will enable a higher throughput rate to be attained during the analysis. It is a further object of the present invention to provide a device which is able to be produced simply, quickly and cost-effectively in industrial manufacturing, and operated in reliable fashion.

The achievement of these objectives is embodied in the features of claims 1 and 15, respectively.

Due to its dimensional design, the device advantageously renders possible a short-focal-length focusing and exposure optics, thereby facilitating a high numerical aperture. Moreover, the time constants of the detectors may be clearly reduced, i.e., their upper critical frequencies increased, accompanied simultaneously by a high sensitivity. In addition, in the context of the device according to the present invention, both the detector-induced dead times, as well as experimental retrofitting of the spectrometers are reduced.

Further advantageous features of the present invention are derived from the dependent claims.

The optical spectroscopy device according to the present invention includes at least one light source and at least one spectrometer produced as an integrated spectrometer, the optical components of the at least one spectrometer being optical microcomponents which are applied integratively to the top and/or bottom side of a substrate board. For the present invention, it is unimportant whether the light source and the spectrometer are regarded as separate units, or whether the light source is regarded as a component of the spectrometer.

In the method according to the present invention for manufacturing an optical spectroscopy device, at least one light source is mounted on a substrate board and at least one spectrometer is produced in a three-dimensional integration on the substrate board. In this context, the at least one spectrometer is assembled from optical microcomponents. In addition, the at least one spectrometer may be produced using additive lithography.

In one preferred specific embodiment of the present invention, the optical microcomponents are applied monolithically to the substrate board. The optical microcomponents may also be applied using additive lithography.

In another preferred embodiment of the present invention, the substrate board has a plurality of light-transmitting regions. In addition, the at least one spectrometer includes a focusing lens mounted on the bottom side of the substrate board for focusing a first light beam radiated by the light source. Also provided on the bottom side of the substrate board is a collective lens for converging a second light beam onto a dispersive element mounted on the top side of the substrate board and onto a detector assigned to the substrate board. By combining focusing and collective lenses, the need for a beam-sorting diaphragm is advantageously eliminated.

It is particularly beneficial that the at least one spectrometer is able to have a first deflecting element, mounted on the top side of the substrate board, for deflecting the first light beam coming from the light source to a focusing lens mounted on the bottom side of the substrate board. The collective lens mounted on the bottom side of the substrate board is used to converge the second light beam onto a second deflecting element, which is mounted on the top side of the substrate board and which deflects the second light beam onto the dispersive element mounted on the top side of the substrate board, and onto a detector that is able to be fabricated lithographically and is mounted on the top side of the substrate board. The first and second deflecting elements are preferably designed in this case as reflecting prisms. The first and second light beams are deflected between a plane disposed in parallel to the substrate board and directions running nearly orthogonally thereto. Due to the small number of refractive surfaces and the folding of the beam out of the horizontal into the direction close to the vertical as a result of total reflection at the reflecting prism, the light loss due to scattering and reflection is kept low.

The dispersive element may be a diffraction grating. Especially preferred is a diffraction grating designed as a phase or echelette grating.

It is also provided in accordance with the present invention to equip at least one spectrometer with a detector array made up of a plurality of detectors.

In one preferred specific embodiment of the present invention, the light source is designed as a miniaturized laser diode that is able to be permanently attached to the substrate board.

It is also especially preferred to mount a plurality of spectrometers integratively side-by-side and/or one behind the other on the substrate board. In this context, the light beam emitted by the light source may be supplied via beam splitters, which are mounted on the top side of the substrate board. However, a plurality of spectrometers, which include a light source, may also be mounted integratively, in rows or in a matrix-type configuration, on the substrate board.

In addition to the above described optical components, one preferred specific embodiment of the present invention may additionally include an array of reaction vessels positioned opposite the bottom side of the substrate board. In this context, the at least one spectrometer and the array of reaction vessels may be positioned essentially in parallel to one another and movably in relation to one another. Also, in this specific embodiment, the spectrometers may be positioned in various geometric configurations, such as in rows.

It is also possible to automate the movement of the spectrometer row and the array of reaction vessels. The device according to the present invention having spectrometers that function in parallel may be manufactured in large quantities using integrative technology and computer-controlled design.

In another specific embodiment, the relative movement of the spectrometer or spectrometer array or spectrometer row is accomplished by a drive having an air bearing system and/or by a sliding table and/or by a piezo-drive.

Figure 2:
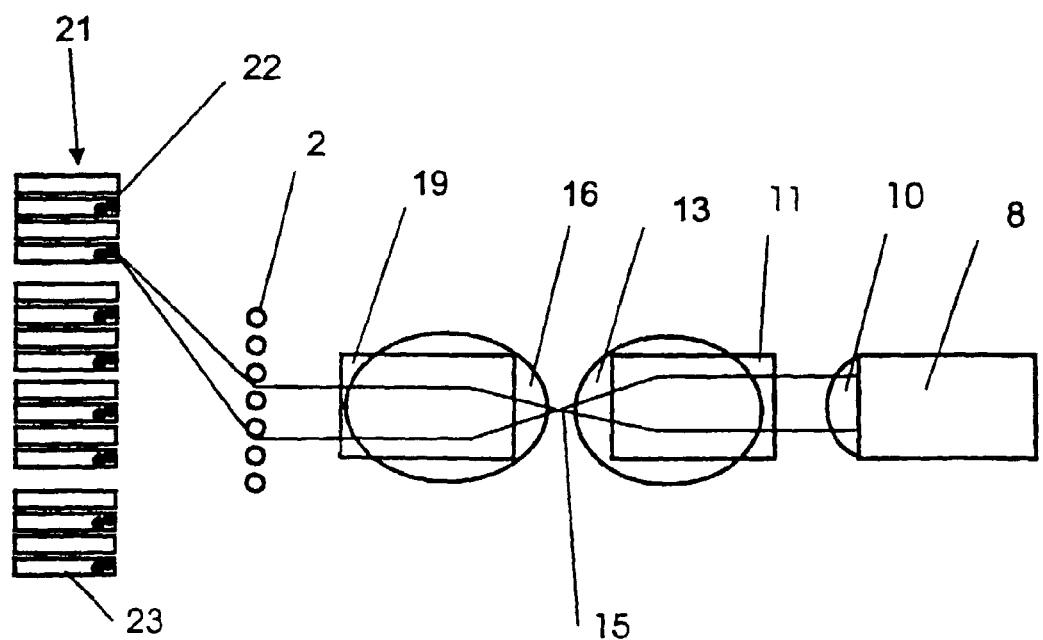
Figure 3:
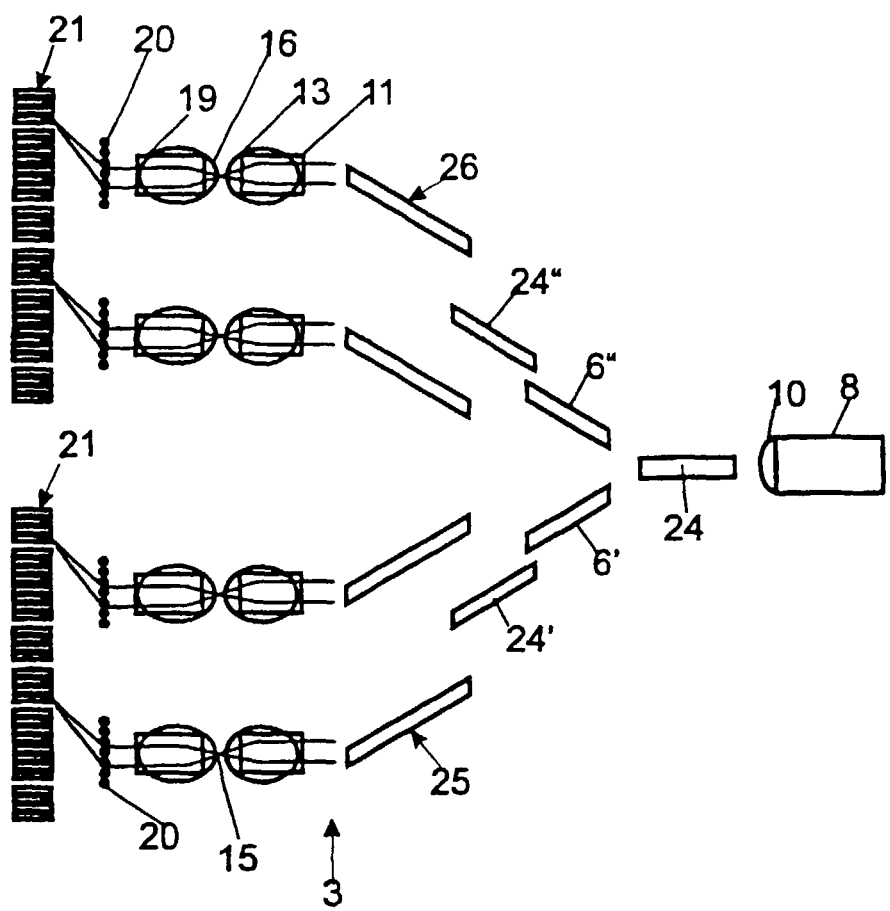

The present invention is elucidated in the following on the basis of the enclosed drawing of a plurality of exemplary embodiments, whose figures show:

FIG. 1 a sectional view of a measuring device having a fluorescence spectrometer according to the present invention;

FIG. 2 a plan view of the fluorescence spectrometer according FIG. 1;

FIG. 3 a plan view of an alternative measuring device according to FIG. 1, four integrated fluorescence spectrometers being provided.

FIG. 1 depicts a measuring device 1 (not shown to scale) having a fluorescence spectrometer 3 that is mounted integratively on a substrate board 2, an array 4 of, for example, six reaction vessels 5 positioned one behind the other, and the corresponding paths of rays 6,7. At this point, it is mentioned that both a plurality of spectrometers 3, as well as a plurality of reaction vessels 5 may be positioned one behind the other, side-by-side, or in a matrix-type configuration. Spectrometer 3 has a light source 8, which is mounted as a miniaturized laser diode 8 on top side 9 of substrate board 2. A beam-shaping aperture optics 10 may be mounted on laser diode 8.

Provided, in addition, on top side 9 of substrate board 2 is a beam-reflecting prism 11 and an illuminating optics 13 mounted at an appropriate position on bottom side 12 of substrate board 2. Illuminating optics 13 is preferably designed as an elliptical focusing lens 13 and includes an aberration correction.

Above focusing lens 13, substrate board 2 has a light-transmitting region 14, preferably a passage 14.

In this context, focusing region 15 (FIGS. 1, 2) of focusing lens 13 used for focusing illuminating beam 10 has a diameter of about 1 μm. In accordance with the present invention, in integrated spectrometer 3, a collective lens 16 is mounted on bottom side 12 of substrate board 2 in such a way that it borders on focusing lens 13. Above collective lens 16, substrate board 2 has a passage 17 for leading through a fluorescence light beam 18 radiated from reaction vessel 5a.

Through this pick-up lens 16 mounted next to focusing lens 13, fluorescent light 18, which is excited by illuminating beam 7, is picked up at a different angle having a high numerical aperture.

An illuminating beam 7 emanating from laser diode 8 of spectrometer 3 is directed via beam-reflecting prism through passage 14 of substrate board 2. Illuminating beam 7 is focused at a reaction vessel 5a, which, for instance, has only a volume of approximately $10^{-6}$ l and which is positioned in reaction vessel array 4 facing bottom side 12 of substrate board 2.

Since the two paths of rays 7, 18 only have region of focus 15 in common, the reaction space is defined by the intersection volume of illuminating light beam 7 and of fluorescence light beam 18 inclined thereto, and is definitively set by the design. In the specific embodiment according to FIGS. 1 and 2, the received fluorescence light 18 is directed by collective lens 16, via a prism 19 working with total reflection, to a dispersive element 20, preferably a diffraction grating.

A plurality of such reaction vessels 5 is preferably combined in a series-type array 4. A chemical reaction in reaction vessel 5a is verified on the basis of a fluorescent emission of one or more attached molecules.

Focusing lens 13 and collective lens 16 are microlenses having surfaces which are capable of being transilluminated and have axes of about 10-100 μm.

In one especially preferred specific embodiment of the present invention, dispersive element 20 is implemented as a phase grating 20 having a free-standing design.

Fluorescent light 18 is diffracted by phase grating 20 in dependence upon the wavelengths, in various directions at a detector array 21. It is advantageous to select the spacing between individual detectors 22 of detector array 21 in coordination with diffraction grating 20, such that a detector 22 is impinged on, at any one time, in focused fashion by one single, well defined wavelength of fluorescent light 18a.

Detectors 22 are preferably designed as free-standing structures and are constructed in an electron beam-induced deposition, where they are placed with a precision of a few nm on a prepared electrical connecting structure in the form of printed conductors 23. In this context, detectors 22 are preferably designed as photoresistors, having a length of about 2 μm and a diameter of about 100-200 nm. The photoresistors are preferably fabricated from nonocrystalline material of, for instance, Au or Pt, in a dielectric carbon matrix.

By positioning the resistors to the exact location and producing the grating constant of phase grating 18, within the scope of the present invention, the detectable wavelengths are definitively set, as they are known from tracer molecules that are excitable to emit fluorescence.

Through the use of phase grating 18, all intensity is directed in one order of diffraction, preferably in the first order of diffraction. In one especially preferred use of an echelette phase grating having a selected design, all diffracted light is directed in only one of two orders of the same order number, so that the maximum fluorescence light signal is obtained. For this, the first order is advantageously selected.

Two spectrometers 3 may also be preferably positioned side-by-side, i.e., in parallel. By adding a beam splitter 24, from light source 8, preferably designed as a laser diode, is split into two beam components to supply parallel spectrometer 3.

In an especially preferred exemplary embodiment according to FIG. 3, two pairs of spectrometers 3 are each supplied with radiation via a beam splitter 24. In this context, also in the case of the illustrated multiple pair-wise array of such spectrometer pairs, the particular path of rays is produced with the aid of beam splitters from the light beam emanating merely from one light source.

It should also be mentioned that the device according to FIGS. 2 and 3 is equivalent to that in FIG. 1 and, therefore, identical or equivalent parts are provided with the same reference numerals By using integrative technology and computer-controlled design, it is possible to manufacture the device having parallel-functioning spectrometers 3 in large quantities. This is advantageously accomplished by a multiple beam splitting. For this, beams 6', 6" emanating from a central beam splitter 24 are directed into two spectrometer branches 25, 26. Provided, in turn, in each of the two spectrometer branches 25, 26, in accordance with the present invention, is a beam splitter 24' and 24", respectively. Beam splitters 24' and 24", respectively, each supply two spectrometers of the type shown in FIGS. 1 and 2.

Within the framework of the present invention, optical components, such as lenses, prisms and/or gratings, are constructed in a computer-controlled process, using a dry resist technique and/or an electron beam-induced deposition. In accordance with the present invention, the positioning of the optical components is adjustable to an accuracy of within a few nm.

The device according to the present invention, i.e., the spectroscopy device manufactured in accordance with the method of the present invention, may essentially be used as follows.

A chemical reaction is verified by the motion, essentially the Brownian motion of the fluorescing molecules attached to at least one of the participating reagents. In the process, the molecular velocity in the reaction product is measured. In accordance with the present invention, this is accomplished by adjusting the measured displacement via an illuminating path predefined by the optics. The time duration of the fluorescence radiation corresponds to the time for which detectors supply a signal induced by monochromatic fluorescent light 18a. In this context, fluorescent light 18a is decomposed by dispersive element 20 according to the wavelength.

From the thus ascertained velocity, the existence of a specific chemical reaction, i.e., the level of already converted reagents may be determined.

Spectrometer 3 or an array of spectrometers may also be assigned to an array of reaction vessels 4. In an array 4 of up to a few hundred reaction vessels 5, 5a, for instance, every second one may have a spectrometer 3 facing opposite it, so that every second reaction vessel 5a may be read out simultaneously. The two arrays may also be moved in relation to one another, and, in this manner, reaction vessels 5 that are not yet measured may be positioned in front of the corresponding spectrometers 3 for measuring purposes.

It is then possible to query the desired reaction via a detector read-out. The detector read-out may also be preferably performed as a computer-controlled operation. In one preferred specific embodiment of the present invention, the detectors used, in which an optically sensitive material is a 0-dimensional electron gas, yield a high upper critical frequency. In these materials, only hopping, as a mechanism of electrical conduction, determines the signal transfer. In a 0-dimensional electron gas of this kind, the energy levels are separated at room temperature to a greater degree than the thermal energy $k_B T$, $k_E$, being the Boltsmann constant. Thus, at room temperature (>27 meV), the photoresistors preferably used are especially low-noise.

The fluorescence radiation is verified by reading out the photocurrent at detector 22 designed as a photoresistor. By introducing an absorber layer 25 to bottom side 12 of substrate board 2, it is beneficially achieved that only the intensity striking into the lens aperture attains detector array 21 of spectrometer 3. It is likewise achieved that adjacent detectors 22 are not influenced. Due to the small size of detectors 22, a plurality of detectors 22, preferably up to a few hundred, may be implemented in one array 21.

The present invention is not limited to the described exemplary embodiments, which may be modified in a multiplicity of ways.

The multiple illumination and spectrometry systems may also each be equipped with only one detector 22 for the light of the wavelength of a specific fluorescing substance subsequent to diffraction grating 20. Thus, all reactions, which are able to be marked by only one specific fluorescent molecule, may be analyzed using this system. The result is a considerable simplification of the evaluation electronics, since only one photoresistor is set up and employed at a specific location. In this type of detector array 21, a limited resolution of spectrometer 3 suffices, which lowers the quality required of focusing 15 and of diffraction grating 20.

In accordance with the present invention, the light supply and the array of dispersive elements 20 may be positioned such that they are inclined from above toward substrate board 2, or inclined away from this board. This means that laser diode 8 is secured to a separate holder over the board, but beam-reflecting prism 11 for deflecting beam 6 is eliminated and is only replaced by a reflection-reducing layer for entry of the light into substrate board 2. In this context, diffraction grating 20 is mounted such that it lies directly on board surface 9 and likewise on a reflection-reducing layer to improve passage of fluorescent light 18. Array 21 of photodetectors 22 is then likewise mounted on a separate board above substrate board 2, requiring a special, precise adjustment of laser diode 8 and of detectors 22.

To achieve an especially high spectral resolution in the fluorescent light, it is also possible to use a combination of prisms and gratings, or also other spectrometers made, for example, of photonic crystals.

Laser diode 8 emitting the exciting light may be provided as an individual diode in the spectrometer or in the device. In this context, it is also conceivable to integrate laser diode 8 monolithically with substrate board 2. The laser diodes may be battery-operated.

Also implicit in the present invention is, that, in a parallel configuration of a plurality of spectrometers 3 or devices, substrate boards 2 are kept separately from one another, or also connected to one another. In addition, the present invention also includes the implementation of a plurality of spectrometers 3, which are able to be positioned in a series- or matrix-type array on a shared substrate board.

It is also provided for a laser diode 8 to be mounted as a power diode having beam-splitting multiple couplers in multimode waveguide technology, on central substrate board 2 supporting the prisms and lenses. In addition, it is provided to distribute the light with equal intensity into individual reaction vessels 5, 5a. Using this technique, it is possible to simultaneously supply 1, 2, 4, 8, 16, etc. parallel devices or spectrometers with light of the same intensity, thereby multiplying the rate at which the reactions to be analyzed are able to be assessed.

The detector read-out may also take place, for example, via an infrared signal output. To improve the signal-to-noise ratio, a preferably miniaturized chopper may be provided in the illuminating beam, in order to operate, for example, a lock-in amplifier mounted on the detector side.

Combining, replacing, or supplementing the described specific embodiments with other additional, generally customary optical components, such as excitation light sources or detectors and the like, is to be considered, moreover, as included within the scope of the present.

Finally, it is understood that the individual features of the present invention may also be used in combinations other than those described or presented.

What is claimed is:

1. A device for use in optical spectroscopy, comprising:
at least one light source; and
at least one spectrometer, wherein the at least one light source and the at least one spectrometer are fabricated integratively, the optical components of the at least one spectrometer being optical microcomponents which are mounted integratively on at least one of a top side and a bottom side of a substrate board, wherein the at least one spectrometer includes:
a focusing lens mounted on the bottom side of the substrate board for focusing a first light beam radiated by the light source onto at least one reaction vessel-underneath the substrate board;
a collective lens mounted on the bottom side of the substrate board for converging a second light beam emanating from the reaction vessel onto a dispersive element mounted on the top side of the substrate board; and
at least one detector assigned to the dispersive element;
the substrate board having a light-transmitting region above the focusing lens and the collective lens,
wherein the optical microcomponents are mounted monolithically on the substrate board.

2. The device as recited in claim 1, wherein the substrate board has a plurality of light-transmitting regions; and the at least one spectrometer includes:
a first deflecting element, mounted on the top side of the substrate board, for deflecting the first light beam coming from the light source to a focusing lens mounted on the bottom side of the substrate board;
a collective lens mounted on the bottom side of the substrate board for converging a second light beam onto a second deflecting element, which is mounted on the top side of the substrate board and which deflects the second light beam onto a dispersive element mounted on the top side of the substrate board;
and a lithographically fabricated detector mounted on the top side of the substrate board.

3. The device as recited in claim 1, wherein the dispersive element is a diffraction grating.

4. The device as recited in claim 3, wherein the diffraction grating is designed as one of a phase and an echelette grating.

5. The device as recited in claim 3, wherein the at least one spectrometer contains a detector array made up of a plurality of detectors.

6. A device for use in optical spectroscopy, comprising:
at least one light source; and
at least one spectrometer, wherein the at least one light source and the at least one spectrometer are fabricated integratively, the optical components of the at least one spectrometer being optical microcomponents which are mounted integratively on at least one of a top side and a bottom side of a substrate board, wherein the at least one spectrometer includes:
a focusing lens mounted on the bottom side of the substrate board for focusing a first light beam radiated by the light source onto at least one reaction vessel-underneath the substrate board;
a collective lens mounted on the bottom side of the substrate board for converging a second light beam emanating from the reaction vessel onto a dispersive element mounted on the top side of the substrate board; and
at least one detector assigned to the dispersive element;
the substrate board having a light-transmitting region above the focusing lens and the collective lens,
wherein the optical microcomponents are applied using additive lithography.

7. The device as recited in claim 6, wherein the light source is designed as a miniaturized laser diode that is permanently attached to the substrate board.

8. The device as recited in claim 6, wherein a plurality of spectrometers are mounted integratively at least one of side-by-side and one behind the other on the substrate board, and the light beam emitted by the light source is able to be supplied via at least one beam splitter mounted on the top side of the substrate board, to the spectrometers.

9. The device as recited in claim 6, wherein a plurality of spectrometers are mounted integratively at least one of side-by-side and one behind the other on the substrate board, a light source being assigned to each spectrometer.

10. The device as recited in claim 6, wherein positioned underneath the substrate board is an array of reaction vessels.

11. The device as recited in claim 10, wherein the at least one spectrometer and the array of reaction vessels are positioned essentially in parallel to one another and movably in relation to one another.

12. The device as recited in claim 11, wherein the device is designed such that the relative movement of the array and of the at least one spectrometer is accomplished by at least one of a drive having an air bearing system, a sliding table, and a piezo-drive.

13. A method for manufacturing an optical spectroscopy device, comprising:
mounting at least one light source on a substrate board;
producing at least one spectrometer in a three-dimensional integration on the substrate board, the at least one spectrometer being assembled from optical microcomponents,
wherein the optical spectroscopy device includes: at least one light source; and at least one spectrometer, wherein the at least one light source and the at least one spectrometer are fabricated integratively, the optical components of the at least one spectrometer being optical microcomponents which are mounted integratively on at least one of a top side and a bottom side of a substrate board, wherein the at least one spectrometer has: a focusing lens mounted on the bottom side of the substrate board for focusing a first light beam radiated by the light source onto at least one reaction vessel-underneath the substrate board, a collective lens mounted on the bottom side of the substrate board for converging a second light beam emanating from the reaction vessel onto a dispersive element mounted on the top side of the substrate board, and at least one detector assigned to the dispersive element; the substrate board having a light-transmitting region above the focusing lens and the collective lens, wherein the optical microcomponents are mounted monolithically on the substrate board.

14. The method as recited in claim 13, further comprising: producing the at least one spectrometer using additive lithography.

15. The method as recited in claim 13, further comprising: designing the at least one light source as a miniaturized laser diode.

16. The method as recited in claim 13, further comprising: mounting integratively at least a second spectrometer with the at least one spectrometer at least one of side-by-side and one behind the other on the substrate board, wherein the light beam emitted by the light source is able to be supplied via at least one beam splitter mounted on the top side of the substrate board, to the spectrometers.

17. The method as recited in claim 13, further comprising: mounting integratively at least a second spectrometer with the at least one spectrometer at least one of side-by-side and one behind the other on the substrate board, at least a second light source being assigned to the at least a second spectrometer.

18. The method as recited in claim 13, wherein the at least one reaction vessel is an array of reaction vessels positioned underneath the substrate board, and the at least one spectrometer and the array of reaction vessels are positioned essentially in parallel to one another and movably in relation to one another.

19. The method as recited in claim 18, further comprising: designing the device such that the relative movement of the at least one spectrometer and the array of reaction vessels is effected by at least one of a drive having an air bearing system, a sliding table, and a piezo-drive.

\* \* \* \* \*